(12) United States Patent
Tsaur (10) Patent No.: US 7,879,780 B2
(45) Date of Patent: *Feb. 1, 2011

(54) STABLE CLEANSING COMPOSITIONS CONTAINING FATTY ACYL ISETHIONATE SURFACTANT PRODUCTS HAVING MORE THAN 10 WT. % OF FATTY ACID/FATTY SOAP CONTENT USING HIGH LEVEL OF POLYOL AND METHODS THEREOF

(75) Inventor: Liang Sheng Tsaur, Norwood, NJ (US)

(73) Assignee: Conopco, Inc., Englewood Cliffs, NJ (US)

( * ) Notice: Subject to any disclaimer, the term of this patent is extended or adjusted under 35 U.S.C. 154(b) by 100 days.

This patent is subject to a terminal disclaimer.

(21) Appl. No.: 12/235,955

(22) Filed: Sep. 23, 2008

(65) Prior Publication Data

US 2010/0075881 A1 Mar. 25, 2010

(51) Int. Cl.
*A61K 7/50* (2006.01)
(52) U.S. Cl. .................. 510/130; 510/156; 510/424; 510/426; 510/428; 510/499
(58) Field of Classification Search .................. None
See application file for complete search history.

(56) References Cited

U.S. PATENT DOCUMENTS

| | | | |
|---|---|---|---|
| 3,723,325 A | 3/1973 | Paran | |
| 4,565,647 A | 1/1986 | Llenado | |
| 5,009,814 A | 4/1991 | Kelkenberg et al. | |
| 5,132,037 A | 7/1992 | Greene et al. | |
| 5,234,619 A | 8/1993 | Greene et al. | |
| 5,290,471 A | 3/1994 | Greene et al. | |
| 5,372,751 A | 12/1994 | Rys-Cicciari et al. | |
| 5,389,279 A | 2/1995 | Au et al. | |
| 5,415,810 A | 5/1995 | Lee et al. | |
| 5,716,919 A | 2/1998 | Sano | |
| 5,739,365 A | 4/1998 | Briody et al. | |
| 5,952,286 A | 9/1999 | Puvvada et al. | |
| 6,077,816 A | 6/2000 | Puvvada et al. | |
| 6,429,177 B1 | 8/2002 | Williams et al. | |

(Continued)

FOREIGN PATENT DOCUMENTS

EP  0 479 795 A1  7/1994

(Continued)

OTHER PUBLICATIONS

XP-002474464, Oct. 1988, English abstract of JP 1987-0077976(based on JP 63-24300).

(Continued)

*Primary Examiner*—Necholus Ogden, Jr.
(74) *Attorney, Agent, or Firm*—Ronald A. Koatz (57) ABSTRACT

The invention provides liquid cleanser compositions which contain fatty acyl isethionates surfactant products having at least 10 wt. % free fatty acid and/or fatty acid soap as the primary surfactant at a level at least 40 wt. % of total fatty acyl isethionate and synthetic cosurfactants in the liquid composition. The key is use of 10% to 60% glycerin and/or sorbitol which has been found, quite unpredictably, to stabilize compositions containing products of such high fatty acid and/or fatty acid soap content.

5 Claims, 2 Drawing Sheets

U.S. PATENT DOCUMENTS

| | | |
|---|---|---|
| 2004/0224863 A1 | 11/2004 | Sun et al. |
| 2008/0153727 A1 | 6/2008 | Tsaur et al. |
| 2008/0153729 A1 | 6/2008 | Tsaur et al. |
| 2008/0153730 A1 | 6/2008 | Tsaur et al. |
| 2009/0062177 A1 | 3/2009 | Tsaur |

FOREIGN PATENT DOCUMENTS

| | | |
|---|---|---|
| EP | 1029532 | 8/2000 |
| EP | 1 479 365 | 11/2004 |
| EP | 1237534 B1 | 1/2005 |
| WO | 97/05857 | 2/1997 |
| WO | 99/32069 | 7/1999 |
| WO | 00/21492 | 4/2000 |
| WO | 03/017968 | 3/2003 |
| WO | 2008/074617 | 6/2008 |
| WO | 2008/074617 A | 6/2008 |
| WO | 2009/030594 A1 | 3/2009 |
| WO | 2009/077495 A2 | 6/2009 |

OTHER PUBLICATIONS

International Search Report on Application No. PCT/EP2008/060835 dated Jan. 26, 2009 (equivalent to related U.S. Appl. No. 11/850,159).

International Preliminary Examination Report on Application No. PCT/EP2007/063128 (equivalent to related U.S. Appl. No. 11/613,617).

Co-pending application: Tsaur; U.S. Appl. No. 11/958,471, filed Dec. 18, 2007.

PCT Search Report and Written Opinion for Intenational Application No. PCT/EP2009/062278, international filed on Sep. 22, 2009, mailed Apr. 16, 2010.

JP 63-243200—Full English translation of previously submitted abstract.

FIG. 1
COMPARATIVE EXAMPLE 1

FIG. 2
EXAMPLE 1

STABLE CLEANSING COMPOSITIONS CONTAINING FATTY ACYL ISETHIONATE SURFACTANT PRODUCTS HAVING MORE THAN 10 WT. % OF FATTY ACID/FATTY SOAP CONTENT USING HIGH LEVEL OF POLYOL AND METHODS THEREOF

FIELD OF THE INVENTION

The invention is directed to personal care skin or hair liquid cleansing compositions and methods of stabilizing. In particular, it relates to such personal care skin or hair cleansing compositions comprising fatty acyl isethionate surfactant product as the primary component at a level of at least 50 wt. % of total fatty isethionate surfactant product and other synthetic co-surfactants in the personal skin or hair liquid cleansing compositions. Commercially available fatty acyl isethionate surfactant products comprise a mixture of fatty acyl isethionates and free fatty acid/fatty acids soaps. The subject invention is directed to fatty acyl isethionate surfactant products having a defined range (starting at about 10%) of fatty acid/fatty soaps in the surfactant product, so total fatty acid in the isethionate surfactant product will always comprise at least 10%, preferably at least 15% by wt.

BACKGROUND OF THE INVENTION

Fatty acyl isethionates (e.g., cocoyl isethionates) surfactant "products" are defined as mixtures of anionic acyl isethionate surfactants and fatty acids/fatty acid soaps. They are highly desirable in personal care skin or hair cleansing products, particularly in personal care products, because they lather well, are mild to the skin and have good emollient properties. Typically, fatty acid isethionate surfactant products are produced by esterification of fatty acids or by reaction of fatty acid chloride having carbon chain length of $C_8$ to $C_{20}$ with isethionate. A typical surfactant product containing fatty acyl isethionate contains about 40 to 95 wt. % acid isethionate, and 5 to 50 wt. %, typically 10 to 40 wt. % free fatty acid, in addition to isethionate salts, typically at less than 5%, and trace (less than 2 wt. %) of other impurities.

A problem with the ready use of fatty acyl isethionate surfactant products in liquid compositions, i.e., composition wherein the acyl isethionate surfactant product is used as a primary component comprising a level of at least 50% wt. % of total fatty isethionate surfactant product and other synthetic surfactants in the liquid composition, however, is the low solubility of these compounds in water. This is especially true for fatty acyl isethionate surfactant product containing high level of free fatty acid/fatty soaps (10% by wt. or higher) and/or long chain fatty acyl isethionates component (e.g., $C_{14}$ and higher). The fatty acyl isethionate component tends to form insoluble surfactant/fatty acids crystals, with the amount of crystals depending strongly on the storage temperature due to the wide range of dissolution temperatures of these crystals. This in turn results in unstable liquid cleansers which exhibit very thick or very thin consistency at low and elevated temperatures. At low temperature, the liquid composition becomes a semi-solid gel which is difficult to use. At elevated temperature, the liquid composition turns into water-thin liquid which causes phase separation of the product.

It would therefore be of tremendous advantage to have compositions having consistent viscosity at both low and elevated temperatures; as well as a way of manipulating compositional ingredients to ensure such consistent viscosity is obtained and that fatty acyl isethionate products, no matter what their free fatty acid/fatty soap content or their chain lengths, can be readily used as the primary surfactant in a liquid cleanser composition. It has not been readily apparent how to address the problem since there are probably hundreds of ways to increase or decrease viscosity but when the issue is one of maintaining a consistent viscosity, it is difficult to know where to begin. Unpredictably, applicants have found specific compositions which are stable (using high levels of polyol) and processes for making such compositions.

Applicants have now found that the problem of inconsistent viscosity and physical instability for liquid cleansers containing high level of fatty acyl isethionate surfactant products can be resolved by forming viscous surfactant liquid crystals at a temperature at or above the dissolution temperature of these long chain fatty acid and/or fatty acyl isethionate crystals such that the liquid composition has high enough viscosity to ensure stability, said stability being defined by the absence of visible physical separation after two weeks of storage at 45° C. Unpredictably, applicants have found the use of polyol, i.e., glycerin or sorbitol, at a level of at least 10 wt. % in the liquid composition, creates a more consistent viscosity which allows fatty acyl isethionate product, regardless of free fatty acid content or chain length of isethionates, to have more consistent viscosity at low and elevated temperatures and to be storage stable. As noted below in connection with EP 1237534, this is particularly unpredictable in that high level of glycerin has in other compositions, caused phase separation and instability.

Acyl isethionate liquids do exist in the art. U.S. Pat. No. 5,415,810 to Lee et al., for example, discloses compositions comprising fatty acyl isethionates and zwitterionic surfactant (e.g., cocoamidopropyl betaines). The reference does not appear to disclose the fatty acyl isethionate product of the invention (comprising 10 to 50% fatty acid) and, in fact, reference teaches away from use of fatty acids.

U.S. Pat. No. 5,739,365 to Brody et al. and U.S. Publication No. 2004/0224863 both disclose use of synthetic surfactants with ammonium counterion to help solubilize fatty acid isethionate.

U.S. Pat. No. 5,132,037 to Greene et al. (and related U.S. Pat. No. 5,234,619 and U.S. Pat. No. 5,290,471) disclose compositions with $C_8$ to $C_{22}$ acyl isethionates, synthetics, and free fatty acid, preferably $C_{16}$ or higher. There seems to be no disclosure of high temperature stability problems associated with liquids containing high level of fatty acid acyl isethionate product or ways to solve such problems. As seen in Table 3 below, not all compositions are stable at 45° C. storage and it is unpredictable what would have been required to achieve such stability.

U.S. Pat. No. 5,952,286 and U.S. Pat. No. 6,077,816, both to Puvvada, disclose liquid cleansing compositions which may contain acyl isethionates and which comprise soluble, lamellar phase inducing structurant (e.g., branched fatty acid). There appears to be no disclosure of high levels of glycerol or any resultant benefit.

Liquid cleansing compositions containing high level of polyol are well known in the art for various purposes. U.S. Pat. No. 5,716,919 to the Andrew Jergens Company taught the use of polyols at a level of 25 to 80 wt. % in a nonionic surfactant-containing liquid cleanser to enhance the cleanser's mildness, non greasy and clean after wash feels. EP 1029532 of Unilever claims self-preserving liquid cleansing composition using high level of glycerol (30 to 50 wt. %) to lower water activity of the liquid composition. In EP 1237534 patent to Unilever, high glycerin content is desired in liquid cleanser for cleanser mildness. However, the patent showed that high glycerin content destabilized liquid composition comprising sulfosuccinic acid monoester surfactants (lines 5 to 9 page 2). To stabilize the liquid composition of this patent with high level of glycerin, a combination of fatty acid soap and acrylate copolymer was required.

U.S. Pat. No. 6,429,177 to Williams et al. describes a separating multi-phase personal wash composition containing 4 to 20% by wt. of polyol in the composition. The patent discloses polyol together with salt to destabilize liquid composition in order to form bi-phasic liquid cleanser. The use of glycerin as high temperature stabilizer is completely unpredictable.

Applicants filed in December 2006 three cases relating to liquid compositions with crystal modifier systems similar to those of the subject invention (U.S. Ser. No. 11/613,666; U.S. Ser. Nos. 11/613,696 and 11/613,617, each to Tsaur). There was no teaching or suggestion in any of these applications, however, that polyol alone at a level of 10 wt. % or more could be used or would function in compositions where fatty acyl isethionate surfactant product comprises 50% or more of the surfactant system by forming viscous surfactant liquid crystals upon the dissolution of fatty acyl isethionate/fatty acid crystals at elevated temperatures (40° C. or above); or that this would function to stabilize liquids at elevated temperature.

Applicants have also filed a related application, Ser. No. 11/850,159 on Sep. 5, 2007 in which combination of alkylamineoxide, alkylamidoamide or mixtures thereof and a second component (e.g., hydrocarbon oil, ammonium salt) form on elevated temperature stabilization system for acyl isethionate surfactant product. The glycerol stabilization system of the subject invention is not disclosed.

None of the references, alone or together, teach or suggest compositions comprising fatty acyl isethionate surfactant product or use of high level of polyols to provide compositions with product viscosity less sensitive to temperature and stable at elevated temperature storage conditions.

BRIEF SUMMARY OF THE INVENTION

In one embodiment, the present invention relates to novel liquid cleansing compositions containing fatty acyl isethionate surfactant product comprising a level of at least 50% of total fatty acyl isethionate surfactant product and cosurfactant, said composition being stabilized with high level of polyols.

More specifically, the invention comprises a polyol stabilized liquid cleansing compositions comprising:
(a) 8 to 50 wt. %, preferably 10 to 40 wt. % of fatty acyl isethionate surfactant product comprising 10 to 50 wt. % fatty acids and/or fatty soaps and 35 to 85 wt. % fatty acyl isethionate in the said product, said product comprising at least 50% of total surfactant product of item (a) and co-surfactants of item (b) in the liquid composition;
(b) 0 to 15 wt. % of a co-surfactant selected from the group consisting of anionic (excluding fatty acyl isethionate of (a)), amphoteric and nonionic surfactants and mixture thereof wherein the amount of said cosurfactant is 0 to 50 wt. % of total amount of fatty acyl isethionate surfactant product of item (a) and cosurfactant of item (b);
(c) 4 to 20% by wt. of $C_8$ to $C_{20}$ linear fatty acids, $C_8$ to $C_{20}$ linear fatty acid soaps or mixtures thereof, including fatty acids and soaps which are part of component (a); and
(d) 10 to 60 wt. % of polyols (e.g., glycerin, sorbitol or mixtures thereof)
wherein the ratio of fatty acyl isethionate surfactant product of item (a) to cosurfactant of item (b) is in the range from 10 to 0 to 5 to 5; wherein at ambient temperature, said composition contains surfactant and/or fatty acid crystals with dissolution temperature from 30° C. to 50° C. (as determined by optical microscope and DSC method described in the disclosure section); wherein the viscosity of said liquid cleanser composition measured at shear rate of 0.01 $s^{-1}$ is at least 250 Pas, preferably at least 350 Pas at 25° C.; wherein the ratio of the viscosity at 40° C. to the viscosity at 25° C., when measured at 0.01 $s^{-1}$, is at least 0.3, preferably 0.4; wherein said composition is stable (i.e., is physically stable and will not partition as can be visually observed) at 45° C. for at least 2 weeks, and wherein, in the absence of sufficient amount of polyols of (d), said composition has a ratio of viscosity at 40° to that at 25° C. of less than 0.3 and exhibits phase separation, when measured at 45° C., in less than two weeks.

In a second embodiment, the invention relates to a process for making such compositions using fatty acyl isethionate surfactant product, co-surfactant, and the combination of surfactant crystal modifiers as noted above.

These and other aspects, features and advantages will become apparent to those of ordinary skill in the art from a reading of the following detailed description and the appended claims. For the avoidance of doubt, any feature of one aspect of the present invention may be utilized in any other aspect of the invention. It is noted that the examples given in the description below are intended to clarify the invention and are not intended to limit the invention to those examples per se. Other than in the experimental examples, or where otherwise indicated, all numbers expressing quantities of ingredients or reaction conditions used herein are to be understood as modified in all instances by the term "about". Similarly, all percentages are weight/weight percentages of the total composition unless otherwise indicated. Numerical ranges expressed in the format "from x to y" are understood to include x and y. When for a specific feature multiple preferred ranges are described in the format "from x to y", it is understood that all ranges combining the different endpoints are also contemplated. Where the term "comprising" is used in the specification or claims, it is not intended to exclude any terms, steps or features not specifically recited. All temperatures are in degrees Celsius (° C.) unless specified otherwise. All measurements are in SI units unless specified otherwise. All documents cited are—in relevant part—incorporated herein by reference.

BRIEF DESCRIPTION OF THE FIGURES

FIGS. 3A and 3B are DSC trace of Comparative Example 1A and Example 1 of this invention. These two DSC (differential scanning calorimetry) traces show that both samples contain fatty acyl isethionate/fatty acid surfactant crystals with dissolution temperature in the range of 30 to 50° C. FIG. 3B (inventive example) shows the sample has a lower "hump" at 40° C. This is a function of formation of viscous surfactant crystals due to presence of polyols rather than solid crystals which readily dissolve at elevated temperature. The lower hump indicates the greater stability of the composition when using polyols. Conversely, composition of FIG. 3A not have many viscous surfactant crystals (it has more solid crystals, and these readily dissolve), and these compositions will be less stable.

DETAILED DESCRIPTION OF THE INVENTION

The present invention relates to novel liquid cleansing compositions comprising fatty acyl isethionate surfactant product as the primary surfactant at a level at least 50 wt. % of total fatty acyl isethionate surfactant product and cosurfactants in the composition. The compositions are viscous and very stable regardless of the level of free fatty acid/fatty soap of starting fatty acyl isethionate surfactant product (e.g., 10-50% in this invention) or the chain lengths of the fatty acyl isethionates (factors which typically affect stability and viscosity of compositions comprising acyl isethionates, especially at low and elevated temperature).

More specifically, the invention comprises liquid cleansing compositions comprising:

(a) 8 to 50, preferably 10 to 40 wt. % of fatty acyl isethionate surfactant product which contains 10 to 50 wt. % fatty acids and/or fatty soaps and 35 to 85 wt. % fatty acyl isethionate in the said product, said product comprising at least 50% of total surfactant product of item (a) and co-surfactants of item (b) in the liquid composition;

(b) 0 to 15% wt. % of a co-surfactant selected from the group consisting of anionic (excluding fatty acyl isethionate of (a)), amphoteric and nonionic surfactants and mixture thereof wherein the amount of said cosurfactant is 0 to 50 wt. % of total amount of fatty acyl isethionate surfactant product of item (a) and cosurfactant of item (b);

(c) 4 to 20% by wt. of $C_8$ to $C_{20}$ linear fatty acids, $C_8$ to $C_{20}$ linear fatty acid soaps or mixtures thereof, including fatty acids and soaps which are part of component (a); and (d) 10 to 60 wt. % polyols (e.g., glycerin, sorbitol or mixtures thereof)

wherein the ratio of fatty acyl isethionate surfactant product of item (a) to cosurfactant of item (b) is in the range from 10 to 0 to 5 to 5; wherein, at ambient temperature, said composition contains surfactant and/or fatty acid crystals with dissolution temperature from 30° C. to 50° C. (as determined by optical microscope and DSC method described in the disclosure section); the viscosity of said liquid cleanser composition at 0.01 s$^{-1}$ being at least 250 Pas, preferably at least 350 Pas at 25° C.; and the ratio of the viscosity at 40° C. to the viscosity at 25° C., when measured at 0.01 s$^{-1}$, being at least 0.3, preferably 0.4; wherein said composition is stable (i.e., is physically stable and will not partition as can be visually observed) at 45° C. for at least 2 weeks, and wherein, in the absence of sufficient amount of polyols of (d), said composition has a ratio of viscosity at 40° to that at 25° C. of less than 0.3 and exhibits phase separation, when measured at 45° C., in less than two weeks.

The invention is defined in greater detail below.

DEFINITIONS

For purposes of this invention, a fatty acyl isethionate "product" comprises (in addition to other components) both pure fatty acyl isethionates surfactant as well as free fatty acid and/or fatty acid salt.

Fatty Acyl Isethionate Surfactant Product

Compositions of the invention comprise 8 to 50% by wt. fatty acyl isethionate surfactant product with more than 10 wt. %, preferably more than 15 wt. % of free fatty acid/fatty soap in the surfactant product.

Fatty acyl isethionate surfactant are typically prepared by the reaction of an isethionates salt such as alkali metal isethionates and an aliphatic fatty acid having 8 to 20 carbon atoms and Iodine Value (measuring degree of unsaturation) of less than 20 grams (g), for example:

$HOR^1SO_3M + RCOOH \rightarrow RCOOR^1SO_3H$ where $R^1$ is an aliphatic hydrocarbon radical containing 2 to 4 carbons;

M is alkali metal cation or metal ion (e.g., sodium, magnesium, potassium, lithium), ammonium or substituted ammonium cation or other counterion; and R is an aliphatic hydrocarbon radical having 7 to 24, preferably 8 to 22 carbons.

Figure 1:
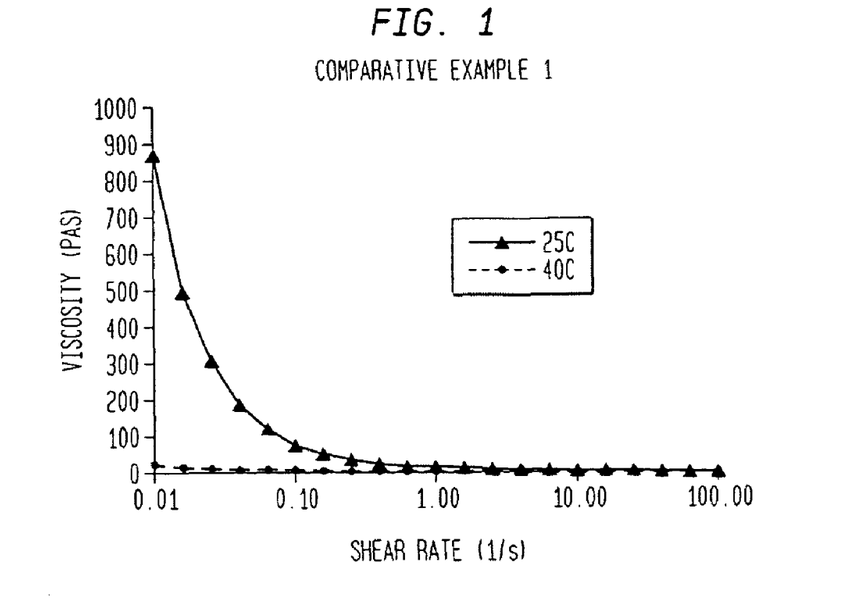
FIG. 1 shows the temperature effect on the viscosity profile of a liquid composition containing only fatty acyl isethionate surfactant product without the elevated temperature stabilizer, i.e., high level of polyols, of this invention (comparative example 1A of Table 3). The figure shows that the sample has a viscosity very sensitive to the storage temperature. At 25° C., it has 875 Pas viscosity measured at shear rate of 0.01 $s^{-1}$ and a lotion-like consistency. At 40° C., it became a water-thin liquid with a viscosity of only 23 Pas at 0.01 $s^{-1}$. The viscosity ratio of 40° C. to 25° C. is 0.023 (i.e., far below 0.3) and the sample showed phase separation at 45° C. storage condition in less than 1 week.
Figure 2:
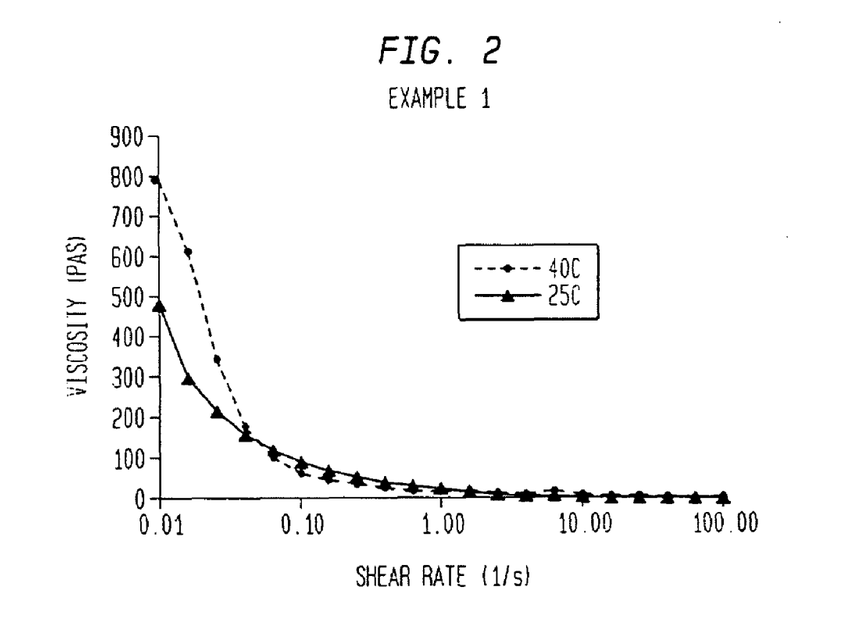
FIG. 2 is a viscosity profile of liquid composition containing fatty acyl isethionate surfactant product at the level same as the one shown in FIG. 1, but with the elevated temperature stabilizer of this invention, i.e. 30 wt. % of glycerin, which is Example 1 of Table 1. Here the sample at 40° C. had a viscosity higher than the one at 25° C., and the viscosity ratio of 40° C. to 25° C. was equal to 1.61. The sample was stable at both ambient temperature (20-25° C.) and at 45° C. for over 4 weeks.
Figure 3A:
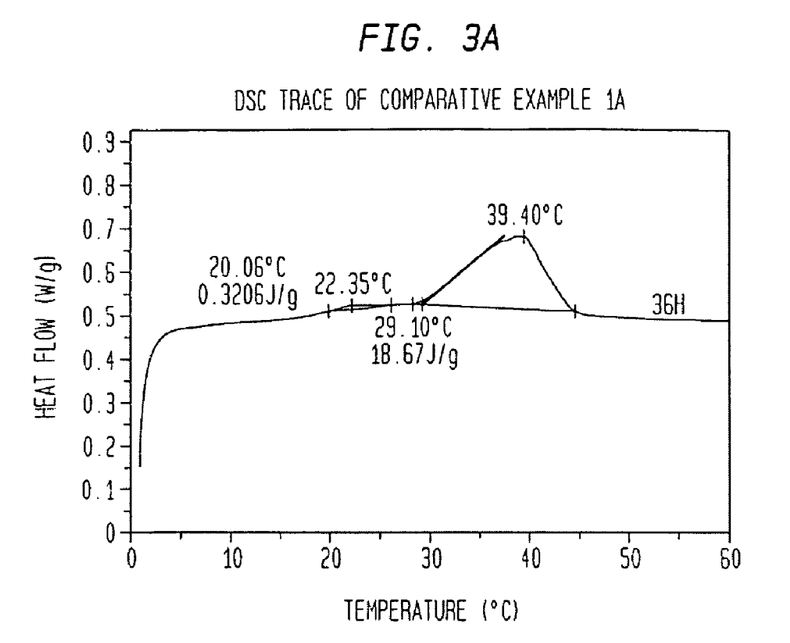
Figure 3B:
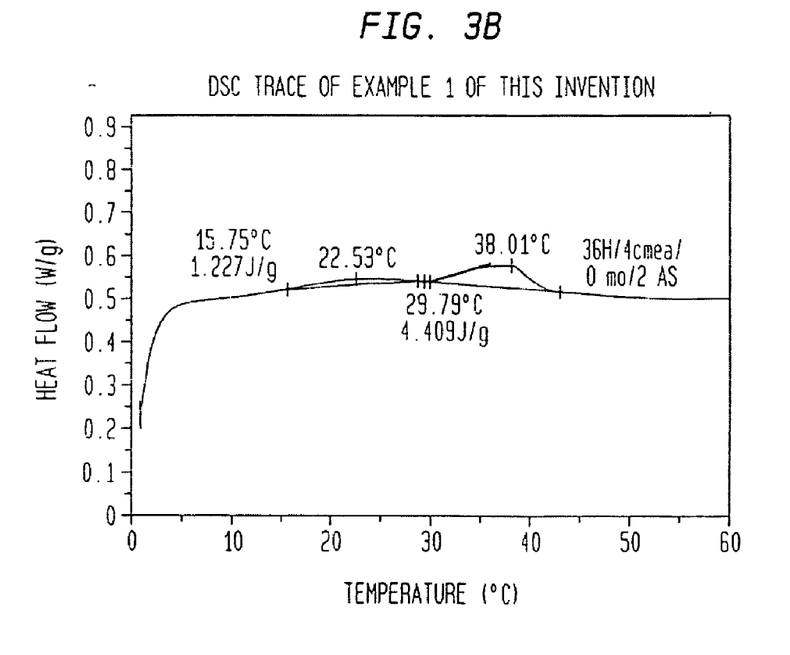

Depending on the processing conditions used, the resulting fatty acyl isethionate product can be a mixture of 45 to 95% by weight of fatty acyl isethionates and 50 to about 0 wt. %, typically 40 to 5 wt. % of free fatty acids, in addition to isethionates salts which are present typically at less than 5 wt. %, and traces (less than 2 wt. %) of other impurities. Generally a mixture of aliphatic fatty acids is used for the preparation of commercial fatty acyl isethionates surfactants; and the resulting fatty acyl isethionate surfactants (e.g., resulting from reaction of alkali metal isethionate and aliphatic fatty acid) have at least 20 wt. % (on basis of fatty acyl isethionates reaction product) of fatty acyl group with 14 or more carbon atoms and at least 16 wt. % of fatty acids with 14 or greater carbon atoms. They form insoluble surfactant crystals in water at ambient temperatures. These fatty acyl isethionate/fatty acid crystals have a dissolution temperature between 30° and 45° C. as shown in FIG. 3 by measuring the crystal transition temperature of an aqueous solution containing only fatty acyl isethionate surfactant product in the liquid with a pH in the range of 6.0 to 7.5 (comparative example 1A of Table 3) using differential scanning calorimetry (DSC) method described below. Due to the presence of these fatty acyl isethionate/fatty acid crystals, liquids containing these commercial fatty acid isethionate products as the primary component (50% or greater of surfactant system) in the liquid composition have very high viscosity at or below room temperature. At or above 40° C., the liquid turns into water thin liquid due to the dissolution of these surfactant crystals as shown in FIG. 1. This causes product inconsistency and storage instability at elevated temperatures (40° C. or above).

A key aspect of the present invention is that the extreme inconsistency of the fatty acyl isethionate surfactant product-containing liquid cleanser and its instability at elevated storage temperatures (40° C. or above) due to the dissolution of insoluble fatty isethionate/fatty acid crystals can be resolved using high level of polyols such that the resulting liquid composition can maintain its consistency and its stability by forming viscous surfactant liquid crystals at elevated storage temperatures (40° C. or above).

Particularly preferred fatty acyl isethionate products with 10 wt. % or more fatty acid/fatty soap which may now be consistently used include DEFI (Direct Esterification of Fatty Isethionate) flakes and synthetic detergent noodles produced from DEFI for personal cleanser application. DEFI flakes typically contain about 65 to 80 wt. % of sodium fatty acyl isethionate and 15 to 30 wt. % free linear fatty acids of 8 to 20, preferably 8 to 18 carbons. More than 65 wt. % of fatty acyl group of the resulting fatty acyl isethionates have 12 to 18 carbon atoms. Dove® cleansing bar noodles are mixtures of DEFI flakes described above and long chain (mainly C16 and C18) fatty acids and fatty soaps which contain about 30 to 60 wt. % of fatty acyl isethionates and 30 to 55 wt. % of fatty acids and fatty soaps. Examples of other commercial fatty acyl isethionate that may be used in the invention are Hostapon® surfactants from Clariant such as Hostapon® SCI65C; Jordapon® CI65; and sodium cocoyl isethionate from Yongan Daily Chemical Co. such as YA-SCI-75® or YA-SCI-65®.

As indicated, these fatty acyl isethionate surfactant products have not typically been used in preparation of personal liquid compositions, particularly those whose fatty acyl isethionate product comprises 50% or greater of surfactant system, because they readily form solid crystals (when used alone and/or with co-surfactant) and consequently make it very difficult to form stable liquids with consistent viscosity at both ambient and elevated temperatures.

The amount of fatty acyl isethionate surfactant product used in the liquid cleanser compositions of the present invention can be in the range of 8% up to 50 wt. %, preferably 10% to 40 wt. % of the liquid composition. The preferred level depends on is the total amount of fatty acyl isethionate surfactant product and other synthetic co-surfactants in the liquid cleanser of the present invention. The amount used should also comprise 50 to 100 wt. % of the total amount of the surfactant system, i.e., the combined fatty acyl isethionate surfactant product and the synthetic co-surfactants described below.

Synthetic Co-Surfactants

A second component of the subject invention are surfactants selected from the groups consisting of anionic surfactants, nonionic surfactants, zwitterionic surfactants, amphoteric surfactants as described below. Such synthetic co-surfactants are believed to partially solubilize fatty acyl isethionate surfactant crystal described above. The amount of synthetic co-surfactant used in the present invention can be in the range of 0 to 15 wt. % in the liquid composition. The amount of co-surfactant in the liquid composition should also be 0 to 50 wt. % preferably 5 to 40 wt. % of total weight of fatty acyl isethionates surfactant product and synthetic co-surfactants of the liquid cleanser composition combined.

The anionic surfactant may be, for example, an aliphatic sulfonate, such as a primary alkane (e.g., $C_8$-$C_{22}$) sulfonate, primary alkane (e.g., $C_8$-$C_{22}$) disulfonate, $C_8$-$C_{22}$ alkene sulfonate, $C_8$-$C_{22}$ hydroxyalkane sulfonate or alkyl glyceryl ether sulfonate (AGS); or an aromatic sulfonate such as alkyl benzene sulfonate.

The anionic may also be an alkyl sulfate (e.g., $C_{12}$-$C_{18}$ alkyl sulfate) or alkyl ether sulfate (including alkyl glyceryl ether sulfates). Among the alkyl ether sulfates are those having the formula:

$$RO(CH_2CH_2O)_nSO_3M$$

wherein R is an alkyl or alkenyl having 8 to 18 carbons, preferably 12 to 18 carbons, n has an average value of greater than at least 0.5, preferably between 2 and 3; and M is a solubilizing cation such as sodium, potassium, ammonium or substituted ammonium. Ammonium and sodium lauryl ether sulfates are preferred.

The anionic may also be alkyl sulfosuccinates (including mono- and dialkyl, e.g., $C_6$-$C_{22}$ sulfosuccinates); alkyl and acyl taurates, alkyl and acyl sarcosinates, alkyl and acyl glycinates, alkyl sulfoacetates, $C_8$-$C_{22}$ alkyl phosphates, alkyl phosphate esters and alkoxyl alkyl phosphate esters, acyl lactates, $C_8$-$C_{22}$ monoalkyl succinates and maleates, and branched acyl isethionates.

The anionic may also be fatty acyl isethionate surfactant product with fatty acid level less than 10 wt. % such as Jordapon CI, which is Na cocoyl isethionate with less than 8 wt. % of fatty acid.

Another class of anionics are carboxylates such as follows:

$$R—(CH_2CH_2O)_nCO_2M$$

wherein R is $C_8$ to $C_{20}$ alkyl; n is 1 to 20; and M is as defined above.

Another carboxylate which can be used is amido alkyl polypeptide carboxylates such as, for example, Monteine LCQ® by Seppic.

Zwitterionic surfactants are exemplified by those which can be broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. A general formula for these compounds is:

$$R^2—Y^{(+)}\underset{\underset{(R^3)_x}{|}}{}—CH_2—R^4Z^{(-)}$$

wherein $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

Amphoteric detergents which may be used in this invention include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula:

$$R^1\underset{}{\overset{\overset{O}{\|}}{-C}}-NH(CH_2)_n\underset{}{\overset{}{\Big]_m}}\underset{\underset{R^3}{|}}{\overset{\overset{R^2}{|}}{N^+}}-X-Y$$

where $R^1$ is alkyl or alkenyl of 7 to 18 carbon atoms;

$R^2$ and $R^3$ are each independently alkyl, hydroxyalkyl or carboxyalkyl of 1 to 3 carbon atoms;

n is 2 to 4;

m is 0 to 1;

X is alkylene of 1 to 3 carbon atoms optionally substituted with hydroxyl, and

Y is —$CO_2$— or —$SO_3$—

Amphoacetates and diamphoacetates are also intended to be covered in possible zwitterionic and/or amphoteric compounds which may be used.

The nonionic which may be used includes in particular the reaction products of compounds having a hydrophobic group and a reactive hydrogen atom, for example aliphatic alcohols, acids, amides or alkyl phenols with alkylene oxides, especially ethylene oxide either alone or with propylene oxide. Specific nonionic detergent compounds are alkyl ($C_6$-$C_{22}$) phenols-ethylene oxide condensates, the condensation products of aliphatic ($C_8$-$C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxides.

The nonionic may also be a sugar amide, such as a polysaccharide amide. Specifically, the surfactant may be one of the lactobionamides described in U.S. Pat. No. 5,389,279 to Au et al. which is hereby incorporated by reference or it may be one of the sugar amides described in U.S. Pat. No. 5,009,814 to Kelkenberg, hereby incorporated into the subject application by reference.

Other surfactants which may be used are described in U.S. Pat. No. 3,723,325 to Parran Jr. and alkyl polysaccharide nonionic surfactants as disclosed in U.S. Pat. No. 4,565,647 to Llenado, both of which are also incorporated into the subject application by reference.

Preferred alkyl polysaccharides are alkylpolyglycosides of the formula $$R^2O(C_nH_{2n}O)_t(\text{glycosyl})_x$$

wherein $R^2$ is selected from the group consisting of alkyl, alkylphenyl, hydroxyalkyl, hydroxyalkylphenyl, and mixtures thereof in which alkyl groups contain from about 10 to about 18, preferably from about 12 to about 14, carbon atoms; n is 0 to 3, preferably 2; t is from 0 to about 10, preferably 0; and x is from 1.3 to about 10, preferably from 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4- and/or 6-position, preferably predominantly the 2-position.

Other surfactants which may be used are described in U.S. Pat. No. 3,723,325 to Parran Jr. and "Surface Active Agents and Detergents" (Vol. I & II) by Schwartz, Perry & Berch, both of which is also incorporated into the subject application by reference.

The invention requires use of 4-20% by wt. $C_8$ to $C_{20}$ linear fatty acids, $C_8$ to $C_{20}$ linear fatty acid soaps or mixtures thereof, including fatty acids and soaps which are part of component (a).

This requirement is intended to clarify that extra linear fatty acids other than those in the acyl isethionate surfactant product of component (a) can be added to achieve high temperature stability of the liquid composition of this invention. As described above, total amount of fatty acids/fatty soaps and its fatty chain length distribution depends on how the acyl isethionate surfactant product is produced. Other than the elevated temperature stabilizer as described below, stability of the liquid composition of this invention also depends on the amount and the composition of these fatty acids/fatty soaps in the liquid composition. For some liquid compositions where low level of acyl isethionate surfactant product or acyl isethionate surfactant product with low level of fatty acid/fatty soap is used, extra fatty acids, especially lauric acid, can be added to achieve elevated temperature stability. Therefore, the total amount of linear fatty acids, linear fatty acid soaps or mixtures thereof in component (a) (where the component would come in as part of the fatty acyl isethionate product) together with that in component (c) combined is at least 4%.

Thus, for example, if the amount of linear fatty acid/fatty acid soap in the acyl isethionate surfactant product (a) has enough linear fatty acid/soap only to provide the cleansing composition with 3% linear fatty acid/fatty acid soap, the minimum 4% of component (c) is to clarify that at least 1% additional linear fatty acid/fatty acid soap (i.e., 3% from the product of (a) and 1% additional) would be added to make 4% minimum in the cleaning composition and as required by (c).

Elevated Temperature Stabilizer

Another essential ingredient of the present invention is the elevated temperature stabilizer. Stabilizer which are used are glycerin and/or sorbitol. The stabilizer(s) is used at a level of 10 wt. % or more in the liquid composition of this invention. As described above, liquid cleansers containing high level (50 wt. % or more) of fatty acyl isethionate surfactant product typically contain solid crystals at ambient temperature (when used alone or with co-surfactants) and consequently make it very difficult to form stable liquids with consistent viscosity at both ambient and elevated temperatures. As shown I Table 3 below, liquid compositions which do not contain the stabilizing polyols either have a viscosity ratio of 40° to 25° C. which is too low; or lack sufficient viscosity to stabilize the liquid during storage. It was both unexpected and unpredictable that the extreme inconsistency of the fatty acyl isethionate surfactant product-containing liquid cleanser and its instability at elevated storage temperatures (40° C. or above), which applicants believe is due to the dissolution of insoluble fatty isethionate/fatty acid crystals, could be resolved using high level of polyols such that the resulting liquid composition could maintain its consistency and its stability (i.e., by forming viscous surfactant liquid crystals at elevated storage temperatures 40° C. or above). Without wishing to be bound by theory, it is believed that the high level of polyol changes the packing of the surfactant mixture of the liquid composition of this invention upon the dissolution of fatty acyl isethionate/fatty acid crystals at a temperature above its dissolution temperature to form viscous surfactant liquid crystal instead of low viscosity surfactant micelles. In this way, the liquid is able to maintain high viscosity and maintain its physical stability.

The total amount of elevated temperature stabilizer, i.e., glycerin and/or sorbitol, in the present invention can be 10 to 60 wt. % of the liquid composition. The desired level of polyol required in the liquid composition of this invention can be determined by measuring the viscosity of the liquid cleanser composition of this invention containing various amount of the elevated temperature stabilizers using the viscosity method described below at both 25° C. and 40° C. The viscosity measured at shear rate of 0.01 $s^{-1}$ should be at least 250 Pas, preferably 350 Pas at 25° C.; and the ratio of the viscosity at 40° C. to the viscosity at 25° C. at 0.01 s$^{-1}$ should be at least 0.3, preferably 0.4. It should be noted that, in the absence of the polyol stabilization system (i.e., if there are not more than 10% polyols), either the ratio of viscosity at 40° to 25° C. is less than 0.3, or the viscosity at 25° C. (measured at 0.01 s$^{-1}$) is less than 250 Pas.

In addition to meeting the viscosity criteria described above, the liquid composition containing the 10 to 60% polyols as noted is stable at 45° C. for over 2 weeks. Besides providing physical stability of the liquid cleanser composition of this invention, the polyols can also enhance the chemical stability of fatty acyl isethionate surfactant at high temperature storage condition. With high level of polyol, especially 25 wt. % or more, hydrolysis of fatty acyl isethionate surfactant in the liquid composition at high temperature storage condition can be reduced due to decrease of water activity in the liquid composition. Thus 25% or more polyol is a preferred embodiment.

Water Soluble/Dispersible Polymers

Water soluble/dispersible polymers are an optional ingredient that is preferred to be included in the liquid composition of the invention. The water soluble/or dispersible polymer can be cationic, anionic, amphoteric or nonionic polymer with molecular weight higher than 100,000 Dalton. These polymers are known to enhance in-use and after-use skin sensory feels, to enhance lather creaminess and lather stability, and to increase the viscosity of liquid cleanser compositions.

Examples of water soluble/or dispersable polymers useful in the present invention include the carbohydrate gums such as cellulose gum, microcrystalline cellulose, cellulose gel, hydroxyethyl cellulose, hydroxypropyl cellulose, sodium carboxymethylcellulose, hydroxymethyl or carboxymethyl cellulose, methyl cellulose, ethyl cellulose, guar gum, gum karaya, gum tragacanth, gum arabic, gum acacia, gum agar, xanthan gum and mixtures thereof; modified and nonmodified starch granules with gelatinization temperature between 30 to 85° C. and pregelatinized cold water soluble starch; polyacrylate; Carbopols; alkaline soluble emulsion polymer such as Aculyn 28, Aculyn 22 or Carbopol Aqua SF1; cationic polymer such as modified polysaccharides including cationic guar available from Rhone Poulenc under the trade name Jaguar C13S, Jaguar C14S, Jaguar C17, or Jaguar C16; cationic modified cellulose such as UCARE Polymer JR 30 or JR 40 from Amerchol; N-Hance 3000, N-Hance 3196, N-Hance GPX 215 or N-Hance GPX 196 from Hercules; synthetic cationic polymer such as MerQuat 100, MerQuat 280, Merquat 281 and Merquat 550 by Nalco; cationic starches, e.g., StaLok® 100, 200, 300 and 400 made by Staley Inc.; cationic galactomannans based on guar gum of Galactasol 800 series by Henkel, Inc.; Quadrosoft Um-200; and Polyquaternium-24.

Gel forming polymers such as modified or non-modified starch granules, xanthan gum, Carbopol, alkaline-soluble emulsion polymers and cationic guar gum such as Jaguar C13S, and cationic modified cellulose such as UCARE Polymer JR 30 or JR 40 are particularly preferred for this invention.

The liquid cleansing composition of the invention also may comprise 0 to 40% by wt. benefit agent.

One class of ingredients is nutrients used to moisturize and strengthen, for example, the skin. These include:
 a) vitamins such as vitamin A and E, and vitamin alkyl esters such as vitamin C alkyl esters;
 b) lipids such as cholesterol, cholesterol esters, lanolin, creaminess, sucrose esters, and pseudo-ceramides;
 c) liposome forming materials such as phospholipids, and suitable amphophilic molecules having two long hydrocarbon chains;
 d) essential fatty acids, poly unsaturated fatty acids, and sources of these materials;
 e) triglycerides of unsaturated fatty acids such as sunflower oil, primrose oil avocado oil, almond oil;
 f) vegetable butters formed from mixtures of saturated and unsaturated fatty acids such as Shea butter;
 g) minerals such as sources of zinc, magnesium, and iron;

A second type of skin benefit agent is a skin conditioner used to provide a moisturized feel to the skin. Suitable skin conditioners include:
 a) silicone oils, gums and modifications thereof such as linear and cyclic polydimethylsiloxanes, amino, alkyl, and alkyl aryl silicone oils;
 b) hydrocarbons such as liquid paraffins, petrolatum, Vaseline, microcrystalline wax, ceresin, squalene, pristan, paraffin wax and mineral oil;
 c) conditioning proteins such as milk proteins, silk proteins and glutens;
 d) cationic polymers as conditioners which may be used include Quatrisoft LM-200 Polyquaternium-24, Merquat Plus 3330-Polyquaternium 30; and Jaguar® type conditioners;
 e) emollients such as esters of long chain fatty acids, such as isopropyl palmitate and cetyl lactate.

A third type of benefit agent is deep cleansing agents. These are defined here as ingredients that can either increase the sense of refreshment immediately after cleansing or can provide a sustained effect on skin problems that are associated with incomplete cleansing. Deep cleansing agents include:
 a) antimicrobials such as 2-hydrozy-4,2',4'-trichlorodiphenylether (DP300) 2,6-dimethyl-4-hydroxychlorobenzene (PCMX), 3,4,4'-trichlorocarbanilide (TCC), 3-trifluoromethyl-4,4'-dichlorocarbanilide (TFC), benzoyl peroxide, zinc salts, tea tree oil,
 b) anti-acne agents such as salicylic acid, lactic acid, glycolic acid, and citric acid, and benzoyl peroxide (also an antimicrobial agent),
 c) oil control agents including sebum suppressants, modifiers such as silica, titanium dioxide, oil absorbers, such as micro sponges,
 d) astringents including tannins, zinc and aluminum salts, plant extracts such as from green tea and Witch-hazel (Hammailes),
 e) scrub and exfoliating particles, such as polyethylene spheres, agglomerated silica, sugar, ground pits, seeds, and husks such as from walnuts, peach, avocado, and oats, salts,
 f) cooling agents such as methanol and its various derivatives and lower alcohols,
 g) fruit and herbal extracts,
 h) skin calming agents such as aloe vera,
 i) essential oils such as mentah, jasmine, camphor, white cedar, bitter orange peel, rye, turpentine, cinnamon, bergamot, citrus unshiu, calamus, pine, lavender, bay, clove, hiba, eucalyptus, lemon, starflower, thyme, peppermint, rose, sage, menthol, cineole, sugenol, citral, citronelle, borneol, linalool, geranoil, evening primrose, camphor, tymol, spirantol, penene, limonene and terpenoid oils.

Other benefit agents that can be employed include anti-aging compounds, sunscreens, and in lightening agents.

The final liquid cleanser composition of the present invention should have a viscosity more than 250, preferably greater than 350 Pas measured at 0.01 rps determined by a Rheometric Scientific SR5 Rheolmeter at 25° C. following the methodology for viscosity determination described below; and pH between 4.0 to 8.0, preferably 4.5 to 7.5. At ambient temperature, the composition contains surfactant/fatty acids crystals with dissolution temperature between 30° C. to 50° C. Presence of the surfactant/fatty acid crystals in the liquid composition of this invention can be confirmed either by an optical microscope or DSC measurement. The compositions should also be physically phase stable at room temperature and 45° C. for at least two 2 weeks.

Other Optional Components

In addition, the compositions of the invention may include 0 to 10% by wt. optional ingredients as follows:

Perfumes; sequestering agents, such as tetra sodium ethylenediaminetetraacetate (EDTA), EHDP or mixtures in an amount of 0.01 to 1%, preferably 0.01 to 0.05%; and coloring agents, opacifiers and pearlizers such as zinc striate, magnesium stearate, $TiO_2$, EGMS (ethylene glycol monostearate) or Lytron 621 (Styrene/Acrylate copolymer); all of which are useful in enhancing the appearance or cosmetic properties of the product.

The compositions may further comprise antimicrobials such as 2-hydroxy-4,2'4' trichlorodiphenyl ether (DP300); preservatives such as dimethyloldimethylhydantoin (Glydant XL 1000), parabens, sorbic acid etc.

EXAMPLES & PROTOCOL

Methodology of Differential Scanning Calorimetry (DSC)

Samples were weighed into an aluminum pan, hermetically sealed, and loaded into a 2920 MDSC machine from TA Instruments at 25° C. The sample was equilibrated to a temperature of 2° C., Iso-Track for 2 minutes followed by heating at 5° C./min to 60° C.

Methodology for Viscosity Measurement

Viscosity was measured using either AR-G2 controlled-stress Rheometer from TA Instruments either with steady rate sweep test method or peak hold test method. Procedures and set up for each test method to measure the cleanser's viscosity are described below:

| Test method A: | Steady Rate Sweep Method |
|---|---|
| Geometry: | Cone and Plate |
| Diameter: | 40 mm |
| Cone Angle: | 2° |
| GAP: | 0.061 mm |
| | Experimental Conditions: |
| Test type: | Steady Rate Sweet |
| Shear Rate Ramp: | from 0.01 to 100 $s^{-1}$ (log mode, 5 points per decade) |
| Measurement Time: | 40 seconds |
| Temperature: | Various (25° C./40° C.) |

Procedure:

About 0.5 g of sample was poured on to the plate. Cone was lowered to the gap of 0.1 mm and excess of sample was removed using plastic spatula. Gap was reduced to 0.061 mm and test was started. Shear rate vs. viscosity were plotted.

| Test method B: | Peak hold method |
|---|---|
| Geometry: | Standard Aluminum parallel plate |
| Diameter: | 40 mm |
| GAP: | 1000 micrometer |
| Test settings: | hold shear rate (1/s) at 0.01 |
| Duration | 50 seconds |
| Sampling delay time: | 10 seconds |
| Temperature: | various (25 c./40 c.) |

Procedure:

About 2 g of sample was poured on to the plate. Plate was lowered to the gap of 1000 micrometer and excess of sample was removed using plastic spatula. Test was started and 5 readings were obtained. $1^{st}$ reading was omitted and averages of last reading were used.

Examples of Compositions of the Invention are Set Forth Below:

TABLE 1

Examples 1 to 7 of this invention

| | Example # | | | | | | |
|---|---|---|---|---|---|---|---|
| | 1 | 2 | 3 | 4 | 5 | 6 | 7 |
| Dove ® noodle | 40 | 30 | 30 | 30 | 30 | 30 | 30 |
| Jordapon Cl prill | — | 5 | 5 | 5 | 0 | 0 | 2 |
| Na lauryl 1EO sulfate | — | — | — | — | 5 | — | 3 |
| Na cocoamido propyl betaine | — | — | — | — | — | 5 | 0 |
| Glycerin | 30 | 10 | 20 | 30 | 30 | 30 | 30 |
| Glydant plus | 0.1 | 0.1 | 0.1 | 0.1 | 0.1 | 0.1 | 0.1 |
| Perfume | 1 | 1 | 1 | 1 | 1 | 1 | 1 |
| Viscosity at 25 C. (Pas at 0.01 $sec^{-1}$) | 30440 | 2730 | 4178 | 5353 | 6448 | 9321 | 6146 |
| Viscosity ratio of 40 to 25 C. | 0.43 | 0.87 | 1.11 | 0.99 | 0.54 | 0.63 | 0.58 |

TABLE 2

Examples 8 to 15 of this invention

| | Example # | | | | | | | |
|---|---|---|---|---|---|---|---|---|
| | 8 | 9 | 10 | 11 | 12 | 13 | 14 | 15 |
| Dove ® noodle | 20 | 20 | 20 | 20 | 16 | 16 | 10 | 10 |
| Jodapon Cl prill | 8 | 0 | 8 | 3 | 6 | 4 | | |
| Na lauryl 1EO sulfate | — | 5 | — | 5 | — | — | 5 | 5 |
| Na cocoamido propyl betaine | — | 3 | — | — | — | 4 | | |
| Na$_2$ lauryl sulfosuccinates | — | — | — | — | — | — | 5 | 5 |
| Lauric acid | 2 | 2 | 2 | — | 1 | 1 | 1.4 | 1.4 |
| Glycerin | 30 | 30 | — | 50 | 60 | 45 | 20 | 30 |
| Sorbitol | — | — | 30 | — | | | — | — |
| Jaguar C13S | — | — | — | — | — | — | 0.5 | 0.5 |
| Glydant plus | 0.1 | 0.1 | 0.1 | 0.1 | 0.1 | 0.1 | 0.1 | 0.1 |
| Perfume | 1 | 1 | 1 | 1 | 1 | 1 | 1 | 1 |
| Viscosity at 25 C. (Pas at 0.01 sec$^{-1}$) | 3529 | 5477 | 1721 | 2112 | 12540 | 1356 | 661 | 3770 |
| Viscosity ratio of 40 C. to 25 C. | 0.49 | 0.45 | 2.49 | 1.44 | 0.45 | 0.62 | 0.76 | 0.64 |

All examples shown in Tables 1 and 2 were prepared by mixing all the ingredients except perfume and glydant plus, EDTA at 70 to 75° C. for 30 to 40 minutes until all the solid ingredients such as Dove® noodle, DEFI flake, and lauric acid dissolved to form an uniform mixture. Perfume, glydant plus (a hydantoin preservative) and other minor ingredients were added after the liquid was cooled below 40° C. The pH of these liquids was adjusted to 6.0 to 7.0 using either 30% citric acid or 25% NaOH solution. Dove® noodles are fatty acyl isethionate products manufactured by Unilever by mixing 50-75% by wt. of DEFI with 25-50% by wt. of long chain ($C_{16}$ to $C_{18}$) fatty acids and fatty soap. Dove® noodles used in examples of Tables 1 and 2 contain about 48 to 52 wt. % of fatty acyl isethionate surfactant and 33 to 37 wt. % of linear fatty acid/fatty soap, in which more than 75% by wt. of these fatty acid/fatty soap have more than 14 carbons. Jordapon CI prill (ex., ICI) is sodium cocoyl isethionate surfactant product containing less than 10 wt. % fatty acids.

Examples 1 to 15 all contain at least 10 wt. % (Examples 14 and 15) up to 40 wt. % (Example 1) of fatty acyl isethionate surfactant products, i.e., Dove® noodle, either with or without other synthetic cosurfactants. Fatty acyl isethionate product in these examples range from 50 wt. % (Example 14 and 15) to 100 wt. % (Example 1) of total fatty acyl isethionate surfactant product and cosurfactants. In all examples, at least 10 wt. % of glycerin or sorbitol is used in the liquid composition. The prepared samples were stored at room temperature and 45° C. up to 4 weeks. At 25° C., all the samples as shown in Table 1 have a viscosity more than 400 Pas at 0.01 s$^{-1}$ and a viscosity ratio of 40° C. to 25° C. measured at 0.01 s$^{-1}$ higher than 0.4. They were stable at both 25 and 45° C. after storage for over 4 weeks, without visible physical separation. These examples indicate that this invention is sufficiently robust to stabilize fatty acyl isethionate surfactant products containing high level of fatty acid/fatty soap (i.e., when used with high level of polyols as defined in this invention). Compositions are consistently stable at both high and low temperature for over 4 weeks regardless of fatty acid content and/or chain length of fatty acyl group).

To illustrate the effect of polyol on both the viscosity and physical stability of the liquid composition of this invention, six comparative examples either without or with (Comparative 4) sufficient amount of polyol as shown in Table 3 were prepared. All the comparative examples were prepared the same way described above. None of these samples were stable at 45° C. for over 2 weeks and showed phase separation in less than 2 weeks due to either too low viscosity ratio at 40° C. to 25° C. (see comparative Examples 1, 2, 5, and 6 and last row of Table 3) or lack of sufficient viscosity at 25° C. (i.e., higher than 250 Pas, see examples 3 and 4) to stabilize the liquid composition. Specifically, Comparative Example 1 and 2 had similar composition as Example 1 and 2, respectively, without any of the elevated temperature stabilizer of this invention. Both Comparative Examples had very high viscosity at 25° C. but very low viscosity at elevated temperature (viscosity ratio of 40° C. to 25° C. less than 0.1). Both liquids were stable at room temperature, but showed phase separation at elevated temperature in less than 2 weeks. Comparative Examples 3 and 4 had composition similar to Examples 14 and 15 with 10% wt. % of fatty acyl isethionate surfactant products. Both have a viscosity ratio of 40° C. to 25° C. higher than 0.30. However, their viscosity at 25° C. was no more than 117 Pas, much less than the preferred minimum liquid viscosity of this invention (350 Pas), even for Example 4 which contains 10 wt. % of glycerin. To achieve the minimum viscosity at RT and the required viscosity ratio of 40° C. to 25° C. for this surfactant system, more than 10 wt. % of glycerin was required as shown in Example 14 of Table 2 with 20 and 30 wt. % of glycerin respectively. These examples show that high level of glycerin can increase the viscosity ratio at 40° C. to 25° C. and can also increase the viscosity of liquid composition at 25° C., especially for liquids containing low level of fatty acyl isethionate surfactant product and high level of co-surfactant.

TABLE 3

Comparative examples

| | Comparative example# | | | | | |
|---|---|---|---|---|---|---|
| | 1 | 2 | 3 | 4 | 5 | 6 |
| Dove bar noodle* | 40 | 30 | 10 | 10 | 24 | 30 |
| Jordopon Cl prill | — | 5 | — | — | — | — |
| Na cocoamido propyl betaine | — | — | 5 | 5 | 8 | 1 |
| Na$_2$ lauryl sulfosuccinate | — | — | 5 | 5 | — | 2 |
| Lauric acid | — | — | 1.4 | 1.4 | — | — |
| Cocomonoethanol amide | — | — | — | — | 3 | 0 |
| Jaguar C13S | — | — | 0.5 | 0.5 | 0.1 | 0 |
| Glycerin | 0 | 0 | 0 | 10 | 6 | 0 |
| Glydant plus | 0.1 | 0.1 | 0.1 | 0.1 | 0.1 | 0.2 |
| Perfume | 1 | 1 | 1 | 1 | 1 | 0.8 |
| Viscosity at 25 C. (Pas at 0.01 sec$^{-1}$) | 15641 | 2107 | 31 | 117 | 410 | 412 |
| Viscosity ratio of 40 C. to 25 C. | 0.036 | 0.09 | 4.15 | 0.33 | 0.031 | 0.021 |

What I claim is:

1. A liquid cleansing composition comprising fatty acyl isethionate surfactant product as the main surfactant component stabilized with high level of polyols, wherein said composition comprises:
   (a) 8 to 50 wt. % of fatty acyl isethionate surfactant product which contains 10 to 50 wt. % fatty acids and/or fatty soaps and 35 to 85 wt. % fatty acyl isethionate in the said product, said product comprising at least 50% of total surfactant product of item (a) and co-surfactants of item (b) in the liquid composition;
   (b) 0 to 15 wt. % of a co-surfactant selected from the group consisting of anionic, amphoteric and nonionic surfactants and mixture thereof wherein the amount of said cosurfactant is 0 to 50 wt. % of total amount of fatty acyl isethionate surfactant product of item (a) and cosurfactant of item (b) and wherein the anionic surfactant noted does not include fatty acyl isethionate surfactant which is part of component (a);
   (c) 4 to 20% by wt. $C_8$ to $C_{20}$ fatty acids, $C_8$ to $C_{20}$ linear fatty acid soaps or mixtures thereof, including fatty acids and soaps which are part of component (a); and
   (d) 10 to 60 wt. % polyol selected from the group consisting of glycerin, sorbitol, and mixtures thereof,
   wherein the ratio of fatty acyl isethionate surfactant product of item (a) to cosurfactant of item (b) is in the range from 10 to 0 to 5 to 5; wherein at ambient temperature, the said composition contains surfactant and/or fatty acid crystals with dissolution temperature between 30° C. to 50° C.; wherein the viscosity of the said liquid cleanser composition at 0.01 s$^{-1}$ is at least 250 Pas, at 25° C.; wherein the ratio of the viscosity at 40° C. to viscosity at 25° C., when measured at 0.01 s$^{-1}$, is at least 0.3; wherein said composition is physically stable and will not partition as can be visually observed at 45° C. for at least 2 weeks, and wherein, in the absence of sufficient amount of polyols of (d) said composition has ratio of viscosity at 40 to 25° less than 0.3 and exhibit phase separation, when measured at 45° C., in less than two weeks.

2. A composition according to claim 1, wherein a fatty acyl isethionate product used in a process for making said composition comprises mixtures of 45-85% fatty acyl isethionate and 15 to 40% free fatty acids.

3. A composition according to claim 1, wherein the viscosity of the liquid cleanser at 0.01 s$^{-1}$ is at least 350 Pas at 25° C.

4. A composition according to claim 1, wherein the ratio of the viscosity at 40° C. to the viscosity at 25° C. at 0.01 s$^{-1}$ is at least 0.4.

5. A process for preparing a stable liquid composition using fatty acyl isethionate surfactants,
   wherein said process comprises combining compounds (a) to (d) below:
   (a) 8 to 50 wt. % of fatty acyl isethionate surfactant product containing 10 to 50 wt. % fatty acids and/or fatty soaps and 35 to 85 wt. % fatty acyl isethionate in the said product, said product comprising at least 50% of total surfactant in product of item (a) and co-surfactant of item (b) in the liquid composition;
   (b) 0 to 15 wt. % of a cosurfactant selected from the group consisting of anionic surfactant, amphoteric surfactant, nonionic surfactants and mixtures thereof wherein the amount of said cosurfactant is 0 to 50 wt. % of total amount of fatty acyl isethionate of item (a) and cosurfactant of item (b) and wherein the anionic surfactant noted does not include fatty acyl isethionate surfactant which is part of component (a);
   (c) 4 to 20% by wt. $C_8$ to $C_{20}$ fatty acids, $C_8$ to $C_{20}$ linear fatty acid soaps or mixtures thereof, including fatty acids and soaps which are part of component (a); and
   (d) 10 to 60 wt. % polyol selected from the group consisting of glycerin, sorbitol, and mixtures thereof,
   wherein the ratio of fatty acyl isethionate surfactant product of item (a) to cosurfactant of item (b) is in the range of 10/0 to 5/5 at ambient temperature, the said composition contains surfactant and/or fatty acid crystals with dissolution temperature between 30° C. to 50° C.; the viscosity of the said liquid cleanser composition at 0.01 s$^{-1}$ is at least 250 Pas, at 25° C.; the ratio of the viscosity at 40° C. to viscosity at 25° C., when measured at 0.01 s$^{-1}$, is at least 0.3; wherein said composition is physically stable and will not partition as can be visually observed at 45° C. for at least 2 weeks, and wherein, in the absence of sufficient amount of polyols of (d) said composition has ratio of viscosity at 40 to 25° less than 0.3 and exhibit phase separation, when measured at 45° C., in less than two weeks.

* * * * *